(12) United States Patent
Bitensky et al.

(10) Patent No.: US 8,071,282 B2
(45) Date of Patent: *Dec. 6, 2011

(54) METHOD OF STORING RED BLOOD CELLS WITH AN ACIDIC ADDITIVE SOLUTION UNDER OXYGEN DEPLETION

(75) Inventors: Mark W Bitensky, Waban, MA (US); Tatsuro Yoshida, West Newton, MA (US)

(73) Assignee: The Trustees of Boston University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/128,576

(22) Filed: May 13, 2005

(65) Prior Publication Data

US 2005/0208462 A1  Sep. 22, 2005

Related U.S. Application Data

(63) Continuation of application No. 10/295,781, filed on Nov. 15, 2002, now abandoned.

(60) Provisional application No. 60/322,405, filed on Nov. 16, 2001.

(51) Int. Cl.
*A01N 1/02* (2006.01)
(52) U.S. Cl. .......................................................... 435/2
(58) Field of Classification Search .................... None
See application file for complete search history.

(56) References Cited

U.S. PATENT DOCUMENTS 5,624,794 A * 4/1997 Bitensky et al. ................. 435/2
5,789,151 A * 8/1998 Bitensky et al. ................. 435/2

FOREIGN PATENT DOCUMENTS

WO  WO 96/29864  * 10/1996

OTHER PUBLICATIONS

Greenwalt et al., "Studies in Red Blood Cell Preservation", Vox Sang. 65 : 87-94 (1993).*
De Angelis et al., "Erythrocyte Shape Control in Stored Blood: The Effect of Additive Solution on Shape Recovery", Haematologica 73: 7-12 (1988).*
Hamasaki et al., "Acid Citrate Dextrose Phosphoenolpyruvate Medium as a Rejuvenant for Blood Storage", Transfusion 23 (10) : 1-7 (1983).*
Valeri et al., "The survival, function and hemolysis of human RBCs stored at 4C in additive solution (AS-1, AS-3 or AS-5) . . . ", Transfusion 40 : 1341-45 (Nov. 2000).*

* cited by examiner

*Primary Examiner* — Sandra Saucier
(74) *Attorney, Agent, or Firm* — Ohlandt, Greeley, Ruggiero & Perle, LLP (57) ABSTRACT

There is provided compositions and methods for the storage of red blood cells. The compositions are additive solutions comprising adenine, dextrose, mannitol, $NaH_2PO_4$, and optionally NaCl and/or $NH_4Cl$. Composition are preferably used with oxygen-depletion refrigerated storage of red blood cells and may optionally be employed with nutrient supplements extending the useful shelf life of stored blood.

10 Claims, 7 Drawing Sheets

METHOD OF STORING RED BLOOD CELLS WITH AN ACIDIC ADDITIVE SOLUTION UNDER OXYGEN DEPLETION

This application claims priority from U.S. Provisional Application No. 60/322,405 filed Nov. 16, 2001.

This application is a continuation of U.S. patent application Ser. No. 10/295,781 filed on Nov. 15, 2002, now abandoned.

This invention was made with partial support from the United States Office of Naval Research, Contract No. N00014-98-1-0451. The Government has certain rights in the invention.

FIELD OF THE INVENTION

The present invention relates to the preservation of blood in liquid form. More particularly, the present invention relates to compositions and methods useful for the storage of red blood cells. Still more particularly, compositions and methods useful for refrigerated storage of red blood cells in oxygen-depleted refrigeration are provided.

DESCRIPTION OF THE PRIOR ART

By way of background, currently the supplies of liquid blood are limited by storage. Stored blood expires after about 42 days of refrigerated storage. Red blood cells may, for example, be stored under refrigeration at a temperature above freezing (4° C.) as packed blood cell preparations. Red blood cells may be concentrated from whole blood with separation of the liquid blood component (plasma). Expired blood cannot be used and is discarded. There are periodic shortages of blood that occur due to donation fluctuation, emergencies and other factors. The logistics of blood supply and distribution impact the military, especially during times of combat, and remote hospitals or medical facilities. There is currently a need for the storage of autologous blood to avoid the significant risks of infection associated with non-autologous donor blood. Patients currently cannot collect and store with current technology enough autologous blood for certain pre-planned surgeries, including hip replacement, organ transplantation and the like.

Storage of frozen blood is known in the art but such frozen blood has limitations. For a number of years, frozen blood has been used by blood banks and the military for certain high-demand and rare types of blood. However, frozen blood is difficult to handle. It must be thawed which makes it impractical for emergency situations. Once blood is thawed, it must be used within 24 hours.

U.S. Pat. No. 4,769,318 to Hamasaki et al. is directed to additive solutions for blood preservation and activation. U.S. Pat. No. 5,624,794 to Bitensky et al. and also U.S. Pat. No. 6,162,396 to Bitensky et al. are directed to the storage of red blood cells under oxygen-depleted conditions. U.S. Pat. No. 5,789,151 to Bitensky et al is directed to blood storage additive solutions.

Additive solutions for blood preservation and activation are known in the art. For example, Rejuvesol (available from enCyte Corp., Braintree, Mass.) is add to blood after cold storage (i.e., 4° C.) just prior to transfusion or prior to freezing (i.e., at −80° C. with glycerol) for extended storage.

In light of current technology, there still remains a long-felt need for the extension of the useful shelf-life of stored liquid blood, especially for extension technology that is relatively inexpensive, easy to handle, and that provides significantly extended long-term storage.

Accordingly, it is an object of the present invention to provide a method for extended storage of red blood cells.

It is another object of the present invention to provide nutrient or metabolic supplements useful with the storage of red blood cells.

Another object of the present invention to provide a method for extending the storage of red blood cells using oxygen-free additive solutions and oxygen removal.

These and other objects and advantages of the present invention and equivalents thereof, are achieved by the methods and compositions of the present invention described herein and manifest in the appended claims.

SUMMARY OF THE INVENTION

In accordance with the objects outlined above and other objects, the present invention provides methods and compositions for the preservation of blood in liquid form, preferably for use with packed red blood cells and oxygen-depleted refrigerated storage. Additive solutions for blood preservation comprise adenine, dextrose, mannitol and di-hydrogen phosphate ion, and optionally sodium chloride and ammonium chloride. Packed red blood cells are obtained by mixing whole blood with anticoagulant solution and concentrated with removal of the plasma to form a mass of packed red blood cells. The method of the invention comprises mixing packed red blood cells with additive solution, OFAS3, reducing oxygen in said suspension of red blood cells, preferably by flushing with inert gas, and storing said red blood cells in oxygen-depleted refrigeration at a temperature of preferably 4° C.

DETAILED DESCRIPTION OF THE INVENTION

In its most general form, the present invention provides additive solutions useful for the storage of red blood cells, preferably oxygen-depleted refrigerated storage, and methods for storing red blood cells comprising use of such additive solutions. The compositions of the invention improve the quality of red blood cells in refrigerated storage, especially when combined with oxygen depletion. Oxygen depletion in known to extend the useful shelf life of refrigerated red blood cells. For example, U.S. Pat. No. 5,624,794 to Bitensky et al., describes a method for reducing oxygen in red blood cell suspensions by flushing with inert gas. Blood storage devices which remove oxygen from stored blood are described in U.S. Pat. No. 6,162,396 to Bitensky et al., and may be used in concert with the compositions and methods of the present invention.

Packed red blood cells may be conveniently prepared by techniques known in the art. Whole blood is collected from a donor and an anticoagulant solution is added. The red blood cells are separated from the plasma component of whole blood and packed concentrated red blood cells are obtained. Additive solution of the invention is then mixed with the packed red blood cells creating a suspension of red blood cells. Oxygen in the cell suspension is then removed, preferably by flushing with inert gas, to approximately 10% or less of the level of oxygen in whole blood.

Preferred concentration ranges of the additive solution of the invention, known as Oxygen Free Additive Solution 3 (OFAS3), are presented in Table 1.

TABLE 1

| Ingredient | Range (mM) |
|---|---|
| Adenine | 0.5-4.0 |
| Dextrose | 50-150 |
| Mannitol | 20-70 |
| NaCl | 0-100 |
| NaH$_2$PO$_4$ | 2-20 |
| NH$_4$Cl | 0-30 |
| Effective Osm | 105 |
| Total Osm | 210-330 |
| Adjusted pH | 5.5-7.7 |
| mL added | 100-300 |
| Final Hct | 30-50 |

A particularly preferred OFAS3 comprises 2 mmole/liter of adenine, 110 mmole/liter of dextrose, 55 mmole/liter of mannitol, 26 mmole/liter of NaCl, 12 mmole/liter of NaH$_2$PO$_4$, with an adjusted pH of about 6.5. Final Hct upon addition is about 40-50; effective Osm 105; total Osm 255. The pH may conveniently be adjusted preferably with NaOH. Other bases may also be used.

The additive solutions of the present invention are preferably used with oxygen-depleted refrigerated storage at a temperature of about 4° C. The additive solutions may also be used with metabolic supplementation to extend the useful shelf life of refrigerated red blood cells.

Metabolic supplementation is used commercially. For example, Rejuvesol is indicated for use at 37° C. and a 1 hour rejuvenation of stored blood just prior to transfusion or just prior to freezing in glycerol. The present invention describes addition of metabolic supplement during refrigerated storage combined with the use of oxygen free additive solution (i.e., OFAS3) and oxygen removal. With this approach, unprecedented results have been obtained. For example, red blood cell storage well beyond the current 6-week limit for 12 or up to 20 weeks at 4° C. with levels of 2-3 DPG and ATP that are above those found in freshly drawn blood. A rationale for this efficacy is suggested or inferred from the fact that in the cold, earlier enzymatic steps of the glycolytic pathway are more seriously impaired than the later enzymatic steps. Thus, by bypassing the earlier enzymatic steps of glycolysis with the addition of metabolic intermediates that directly feed or serve as substrates for the later enzymatic steps, we have been able to significantly boost the production of ATP and 2-3 DPG. The fact that these substrates readily traverse the erythrocyte membrane at cold temperature (i.e., 4° C.) is clearly demonstrated by the experimental results obtained which are presented herein. The use of Rejuvesol in its current formulation does incur the need for a simple wash step prior to transfusion.

Metabolic supplementation of the invention is effected at least once, preferably during oxygen-depleted refrigerated storage (i.e., 4°) of red blood cells (c.f., U.S. Pat. Nos. 5,624,794; 6,162,396), along with oxygen-free additive solution, preferably OFAS3 or modification thereof. Blood units are not warmed. EAS61 and OFAS1 are additive solutions known in the art.

Metabolic supplement is added to refrigerated red blood cells. A first addition is made within 6-10 weeks of storage. A second addition is optionally added within 11-20 weeks of storage.

Metabolic supplement solution composition is presented in Table 2.

TABLE 2

| Ingredient | Concentration (g/unit of addition) |
|---|---|
| Na pyruvate | 0.1-2.0 |
| Inosine | 0.5-3.0 |
| Adenine | 0.01-1.0 |
| Na phosphate dibasic | 0-2.0 |
| Na phosphate monobasic | 0-2.0 |
| pH | 5.5-8.0 |

The concentrations, given in mM units, of various blood additive solutions are presented in Table 3.

TABLE 3

| Ingredient | AS-3 | AS-1 | OFAS1 | EAS61 | OFAS3 |
|---|---|---|---|---|---|
| Adenine | 2.2 | 2 | 2 | 2 | 2 |
| Dextrose | 61 | 122 | 110 | 110 | 110 |
| Mannitol | — | 42 | 65 | 55 | 55 |
| NaCl | 70 | 154 | — | 26 | 26 |
| Na citrate | 20 | — | 20 | — | — |
| Citric acid | 2 | — | — | — | — |
| Na$_2$HPO$_4$ | — | — | — | 12 | 12 |
| NaH$_2$PO$_4$ | 20 | — | 20 | — | — |
| pH | | | 7.2* | 8.3 | 6.5* |
| vol. added (mL) | 200 | | 250 | 200 | 200 |
| final Hct | ~40 | | ~35 | ~40 | ~40 |

*pH adjusted with NaOH

The following Examples are illustrative of the invention and are not intended to be limitative thereof.

Example 1

OFAS3: Effect of pH and Oxygen Depletion on Cellular ATP Levels

Figure 1:
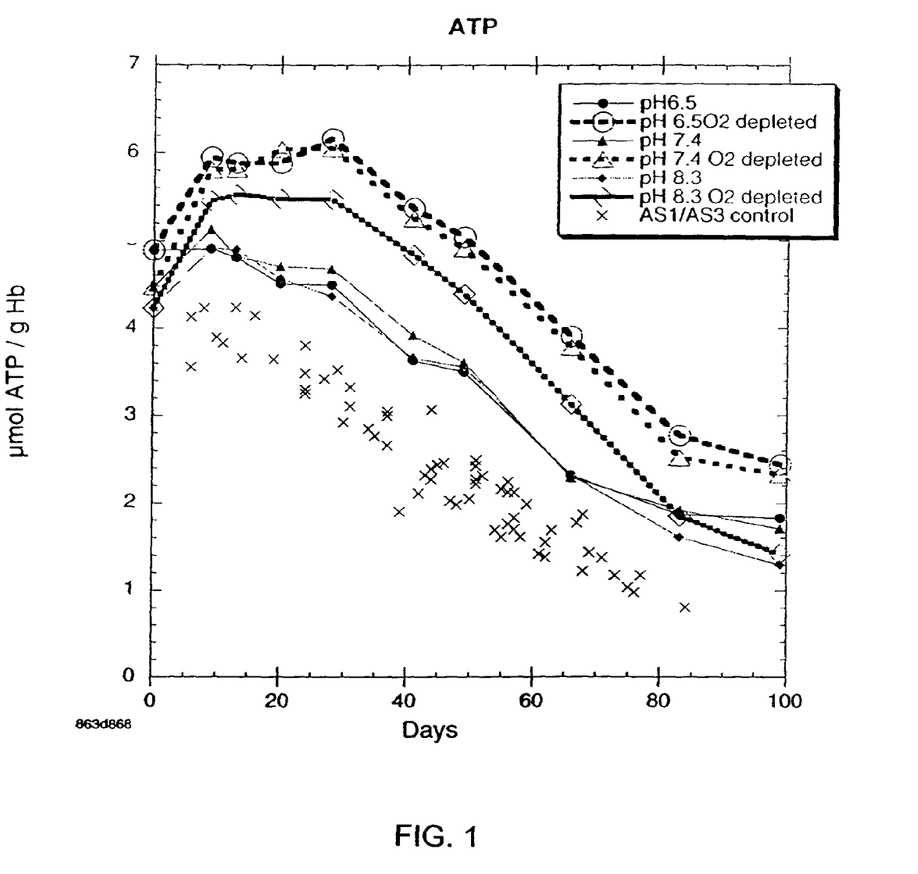
FIG. 1 shows the effect of pH and oxygen depletion on cellular ATP levels of red blood cells in OFAS3.

Results of experimentation to determine the effect of pH and oxygen depletion on cellular ATP levels with blood samples containing oxygen-free additive solution (AFAS3) are presented in FIG. 1. Each point on the graph is the average of 6 subjects. For comparative purposes, AS1 and AS3, the current U.S. standard additive solution, serve as a control. There is a large variability in the values between different test subjects. In order to see the effect of pH, P values (t-test for paired two samples for means) were calculated and are presented in Table 4.

TABLE 4

Pairwise Test of ATP Values
(For Oxygen Depleted Storage at Various pH's)

| Time (Days) | P(T <= t) one-tail pH 6.5 vs. pH 8.3 | P(T <= t) one-tail pH 6.5 vs. pH 7.4 |
| --- | --- | --- |
| 9 | 0.002 | 0.007 |
| 13 | 0.032 | 0.327 |
| 20 | 0.008 | 0.116 |
| 28 | 0.001 | 0.104 |
| 41 | 0.072 | 0.072 |
| 49 | 0.023 | 0.111 |
| 66 | 0.008 | 0.149 |
| 83 | 0.007 | 0.147 |
| 99 | 0.008 | 0.388 |

Although there are large subject to subject variations in ATP levels, there are significant differences between pH 6.5 and pH 8.3. These data show that oxygen depletion further enhances ATP levels as much as 33% by week 3 and 38% by week 14. The increase in ATP levels is dramatically enhanced when red blood cells are stored in oxygen depleted conditions. The best result was obtained with additive solution (AFAS3) at pH 6.5 with oxygen depletion.

Example 2

Figure 2:
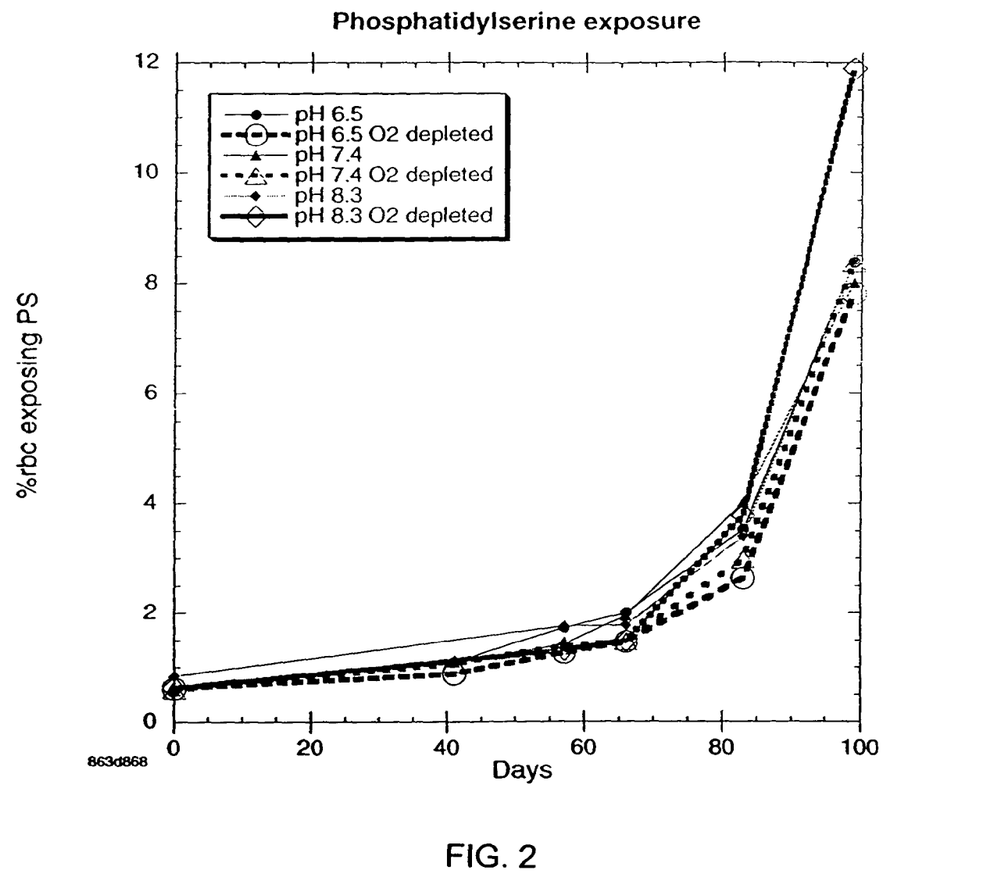
FIG. 2 shows the effect of pH and oxygen depletion on the percentage of red blood cells exposing phosphotidylserine in OFAS3.

OFAS3: Effect of pH and Oxygen Depletion on % of Cells Exposing Phosphatidylserine Results of experimentation to determine the effect of pH and oxygen depletion on the % of red blood cells exposing phosphotidylserine with samples containing oxygen-free additive solution (OFAS3) are presented in FIG. 2. Data were obtained by flow cytometer measurements using FITC-Annexin IV probe. Each point on the graph is the average of 6 subjects. There is a significant reduction in exposed phosophatidylseine after 10 weeks when pH 8.3 and pH 6.5 blood samples, both oxygen depleted, are compared.

Example 3

OFAS3: Effect of pH and Oxygen Depletion on Red Blood Cell Hemolysis

Figure 3:
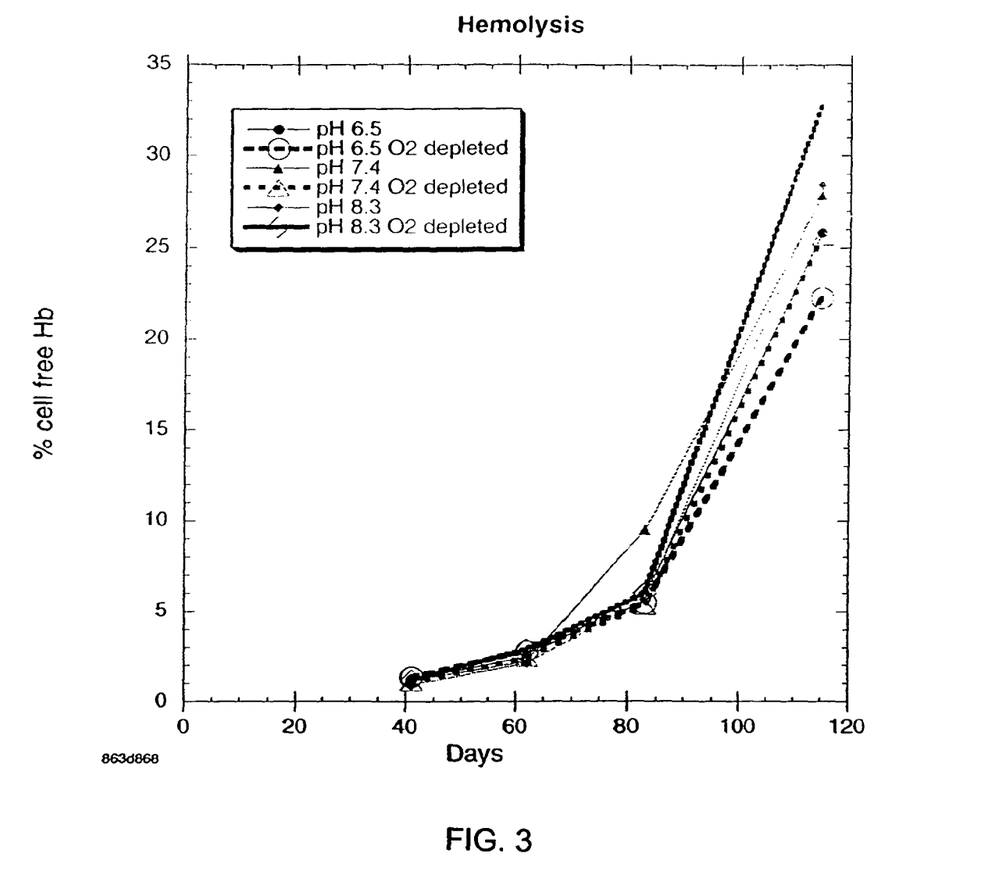
FIG. 3 shows the effect of pH and oxygen depletion on red blood cell hemolysis in cell suspensions in OFAS3.

Results of experimentation to determine the effect of pH and oxygen depletion on red blood cell hemolysis with blood samples containing oxygen-free additive solution (OFAS3) are presented in FIG. 3. Each point on the graph is the average of 6 subjects. Three different pH's were tested, pH 6.5, pH 7.4, and pH 8.3, with control cultures that were not oxygen-depleted. At week 16, the pH 6.5 oxygen-depleted refrigerated red blood cell storage system has the lowest extent of hemolysis.

Example 4

Figure 4:
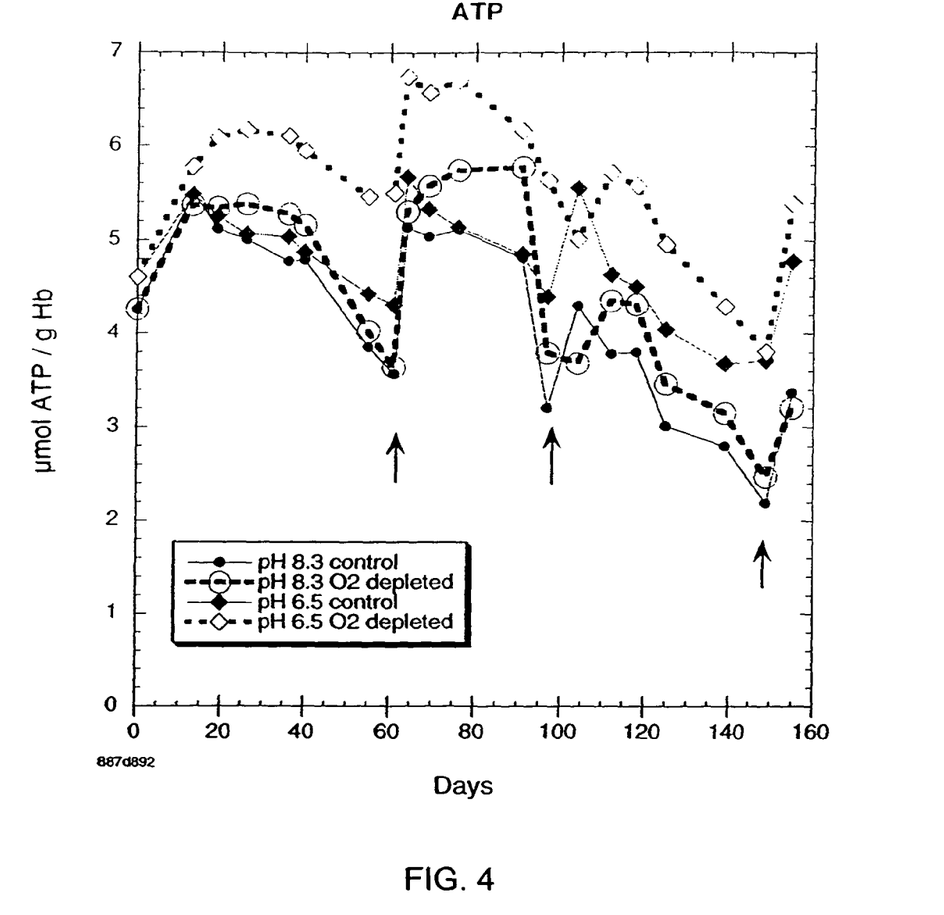
FIG. 4 shows the effect on red blood cell ATP levels of metabolic supplements added at different pH's in the presence or absence of oxygen.

Addition of Metabolic Supplements During Refrigerated, Oxygen-Depleted Red Blood Cell Storage: Effect of Metabolic Supplements Added at Different pH's in the Presence or Absence of Oxygen on Cellular ATP Levels Results of experimentation to determine the effect of addition of metabolic supplements added during refrigerated, oxygen-depleted storage of red blood cells at different pH's in the presence or absence of oxygen on cellular ATP levels, are graphically presented in FIG. 4. Two different pH's were tested, pH 6.5 and pH 8.3, with control cultures that are not oxygen depleted. Metabolic supplement, Rejuvesol, was added to cultures as indicated by the arrows in FIG. 4, which correspond approximately to additions during cold storage at 9, 14, and 21 weeks respectively. These data show that ATP levels are significantly increased each time the cold fuel/metabolic supplement is added. The highest ATP levels are sustained with pH 6.5 additive solution under oxygen depleted conditions. ATP levels are sustained near or above day 0 values throughout 22 weeks of storage with the additions of cold fuel.

Example 5

Figure 5:
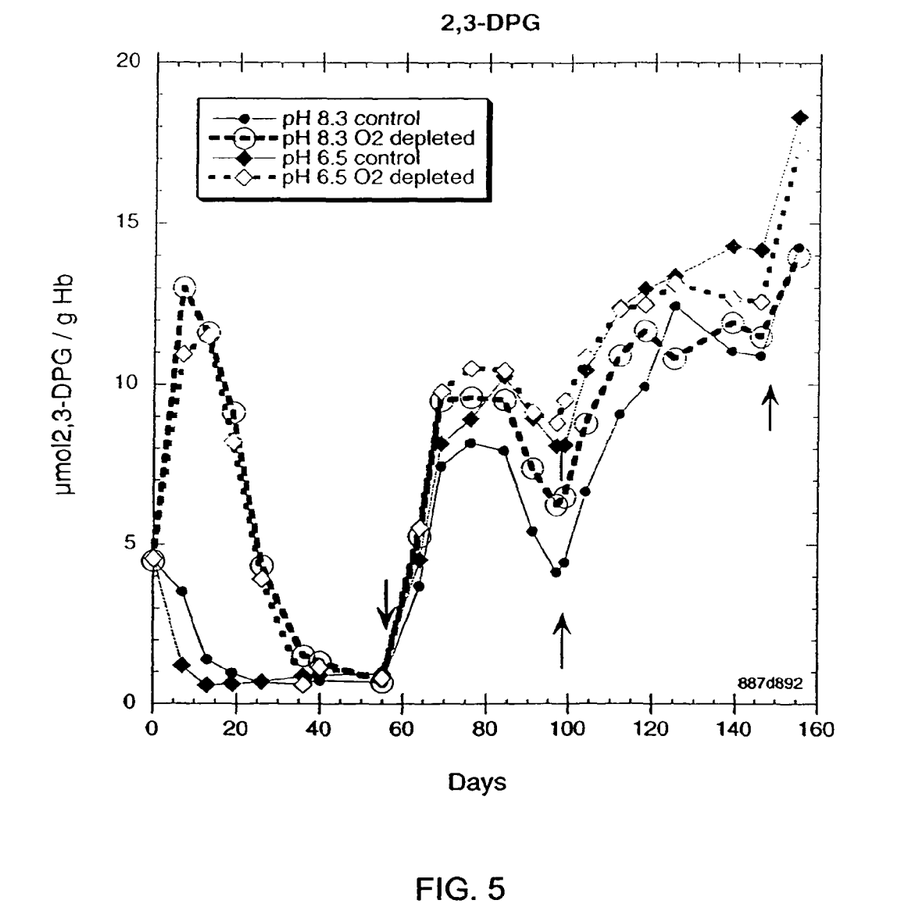
FIG. 5 shows the effect on red blood cell 2,3-DPG levels of metabolic supplements added at different pH's in the presence or absence of oxygen.

Addition of Metabolic Supplements During Refrigerated Oxygen-Depleted Red Blood Cell Storage: Effect of Metabolic Supplements Addition at Different pH's in the Presence and Absence of Oxygen on Cellular 2,3-DPG Levels Results of experimentation to determine the effect of addition of metabolic supplements during refrigerated, oxygen-depleted red blood cell storage in the presence or absence of oxygen on cellular 2,3-DPG levels, are presented in FIG. 5. Each point on the graph is the average of 6 subjects. Two different pH's were evaluated, pH 6.5 and pH 8.3. Control cultures are not oxygen-depleted. Metabolic supplement, Rejuvesol, was added at the time indicated by the arrows, which correspond approximately to 8, 14, and 20 weeks, respectively. These data show that oxygen depletion elevates 2,3-DPG levels significantly at the start of storage, without addition of metabolic supplements. Addition of metabolic supplements increases 2.3-DPG levels slowly at 4° C., and keeps these levels well above day 0 values, thus enhancing oxygen delivery capacity of the transfused blood.

Example 6

Figure 6:
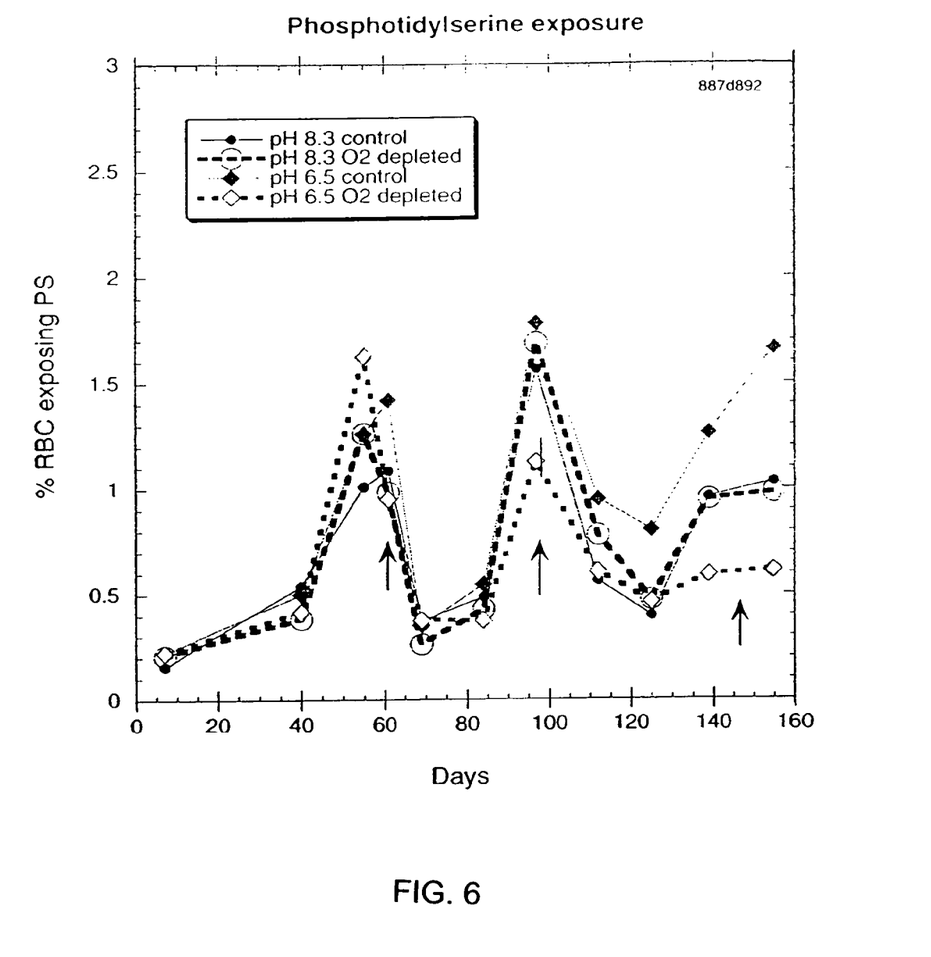
FIG. 6 shows the effect on the percentage of red blood cells exposing phosophatidylserine of addition of metabolic supplements at different pH's in the presence and absence of oxygen.

Addition of Metabolic Supplements During Refrigerated Oxygen-Depleted Red Blood Cell Storage: Effect of Metabolic Supplements Addition at Different pH's in the Presence and Absence of Oxygen on the % of Red Blood Cells Exposing Phosphatidyserine Results of experimentation to determine the effect of addition of metabolic supplements during refrigerated, oxygen-depleted red blood cell storage in the presence or absence of oxygen on the percent of red blood cells exposing phosphatidylserine are presented in FIG. 6. Data were obtained from measurements by flow cytometer using FITC-Annexin IV probe. Each point on the graph represents the average of 6 subjects. Two different pH's were evaluated, pH 6.5 and pH 8.3, with metabolic supplement, Rejuvesol, added at the time indicted by the arrows which correspond to additions at approximately 8.6, 14, and 20 weeks. Control cultures are not oxygen-depleted. Phosphatidylserine is gradually exposed during refrigeration (4° C.). However, addition of metabolic supplements reverses this exposure. This experiment has been repeated three times with similar results. The lowest levels of exposure were seen with a pH 6.5 storage buffer and oxygen depletion.

Example 7

Figure 7:
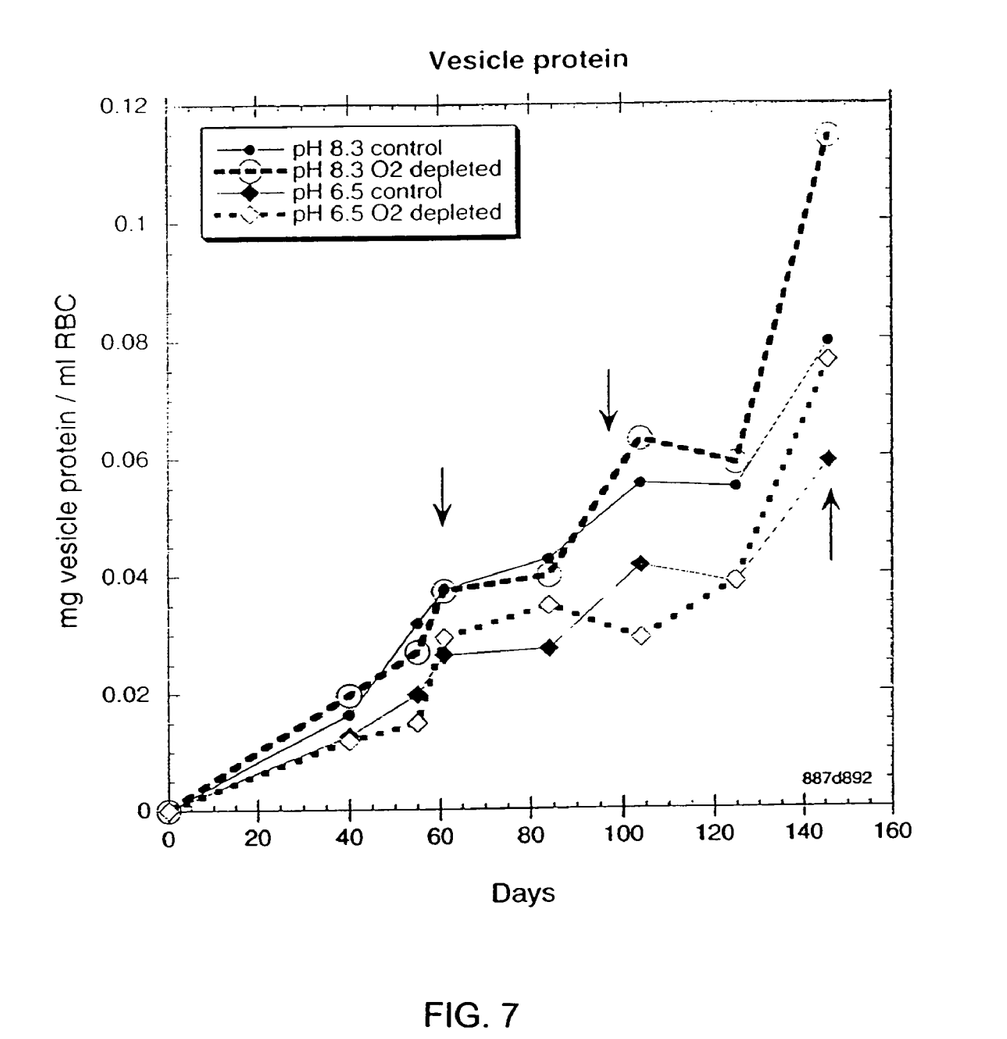
FIG. 7 shows the effect on vesicle protein production of red blood cells of addition of metabolic supplements at different pH's in the presence or absence of oxygen.

Addition of Metabolic Supplements During Refrigerated Oxygen-Depleted Red Blood Cell Storage: Effect of Metabolic Supplements Addition at Different pH's in the Presence and Absence of Oxygen on Vesicle Production Results of experimentation to determine the effect of addition of metabolic supplements during refrigerated, oxygen-depleted red blood cell storage in the presence or absence of oxygen on the vesicle production are presented in FIG. 7. Each point on the graph represents the average of 6 subjects. Two different pH's were evaluated, pH 6.5 and pH 8.3, with metabolic supplement, Rejuvesol, added at the time indicted by the arrows which correspond to additions at approximately 8.6, 14, and 20 weeks, respectively. Control cultures are not oxygen-depleted. It is known that refrigerated red blood cells shed vesicles during storage. Addition of metabolic supplements slows vesicle production. In the system comprising metabolic supplementation during oxygen-depleted refrigerated storage with oxygen-free additive solution, the additive solution OFAS3 was shown to be the most effective of such additives.

Example 8

Twenty-Four-Hour In Vivo Post Transfusion Survival of Stored Red Cell Units

Eight normal subjects each donated a unit of whole blood via a standard, manual method on two separate occasions approximately 8 weeks apart. Subject requirements were the same as those that apply for allogeneic blood donors as established by 21CFR640.3 and the Standards of the American Association of Blood Banks. These units were processed via centrifugation to yield packed red cells via a "soft spin" technique (2000 g*3 min) following holding at room temperature for 1-2 hours, and 200 mL of an experimental additive solution OFAS3 were added (Table 3) to yield a final hematocrit of 35-45%. These and all other manipulations of units involving addition of solutions or sampling were accomplished via a sterile connection device.

The test units were stored in an anaerobic environment following multiple flushes to minimize the oxygen content of each unit using highly purified Ar and $H_2$. Following completion of sampling, the test units were made anaerobic following the procedure provided by the sponsor. Briefly, the units were transferred to a 2000 mL transfer bag using the SCD. Sputtering grade argon was introduced into the unit via a 0.22 micron filter until the transfer bag was completely filled with gas/blood and rotated 10 min at room temperature. Following this hold period, the gas was expelled through the same 0.22 micron filter using a plasma expressor and a vacuum line. This procedure was repeated 6 times, and the unit was transferred to a standard PL146 red cell storage bag with an Ar flush. The unit was then placed in an anaerobic culture jar and 3 exchanges of the contents of the jar were performed with Ar, the last consisting of 2 parts Ar, 1 part scientific grade $H_2$ before the jar was placed in a monitored 4° C. refrigerator. When subsequent samples were taken via the SCD, the storage jar again underwent gas replacement prior to the unit being placed back in the refrigerator. Jars were flushed weekly with Ar if no sampling occurred in that week. Control units were stored in the same refrigerator without altering their gaseous environment.

After 7 weeks of storage, test units underwent a metabolic supplementation using a licensed solution (Rejuvesol, Cytosol Laboratories, Braintree, Mass.); test units underwent an additional metabolic supplementation at 11 weeks (if recoveries to date indicated that continued storage was warranted, vida infra) The contents of the bottle of metabolic supplement were aspirated via needle and syringe and injected via a sampling port into a plastic transfer bag that had been previously flushed with Ar and to which had already been attached a 0.22 micron filter. The solution was then transferred to the unit by sterile docking, and the unit was promptly returned to refrigerated storage (without repeating the gas exchange procedure and without incubation or washing).

Control units were utilized for radiolabeling and autologous reinfusion at 10 weeks; test units were continued in the protocol so long as the prior radiolabeled recovery suggested the continued viability of the cells. In addition, for a radiolabeled recovery to be conducted, the ATP must have been at least 50% of the Day 0 value, and the hemolysis must have been no more than 3.0% at the preceding sampling.

Radiolabe]ing to allow for determination or in vivo red cell recovery' was conducted according to published procedures [J. Nucl. Med. 1975; 16:435-7] 10-20 $\mu CiNa_2^{51}CrO_4$ (Bracco, Princeton, N.J.) were added to a 10 mL aliquot of the unit's cells for 30 min. at room temperature followed by a single double-volume saline wash. [Blood 1871; 38:378-86; Transfusion 1984; 24:109-14] (Prior to labelling, cells from test units were washed four times with a double volume saline wash to remove remaining constituents of the rejuvenation solution.) These cells were injected simultaneously with fresh autologous red cells that had been labeled with 10-20 $\mu$Ci $^{99m}$Tc pertechnetate after 'tinning" to determine the subject's red cell volume; [Dave, R. J., Wallacae, M.e., eds. Diagnostic and investigational uses of radiolabeled blood elements. Arlington: American Association of Blood Banks, 1987] labeled cells were washed once with 40 mL ice-cold saline. Reinfusions were conducted promptly after labeling, and labeled cells were kept on ice until then, Samples were taken from 5 to 30 min. and then at 24 h to determine circulating radioactivity. Red cell volumes were determined by single and double label calculation methods after correction for counting interference and $^{99m}$Tc label elution prior to injection.

Results of a 24-hr in vivo post tranfusion survival study of stored red cell units are presented in Table 5. Hemolysis remained below 1% through 14 weeks of storage. The maximum noted was 1.75% at 16 weeks in one unit.

TABLE 5

| volunteer | A | B | C | D | E | F | G | n | Average | std dev |
|---|---|---|---|---|---|---|---|---|---|---|
| | | | | single label | | | | | | |
| 10 wks test | 73.9 | 74.2 | 69.6 | 72.5 | 64.6 | 81.9 | 90.3 | 7 | 75.3 | 8.4 |
| 12 wks test | 69.9 | 66.9 | 71.6 | 74.3 | | 78.05 | 84.6 | 6 | 74.2 | 6.3 |
| 14 wks test | 65.6 | 61.7 | 58.3 | 79.6 | | 74.2 | 78.8 | 6 | 69.7 | 9.1 |
| 16 wks test | | | | | | 69.7 | 75.1 | 2 | 72.4 | 3.8 |
| 10 wks control | 71.7 | 78.5 | 66.6 | 56.8 | 77.6 | 73.8 | 78.0 | 7 | 71.9 | 7.9 |

TABLE 5-continued

| volunteer | A | B | C | D | E | F | G | n | Average | std dev |
|---|---|---|---|---|---|---|---|---|---|---|
| double label | | | | | | | | | | |
| 10 wks test | 82.6 | 83.5 | 76.7 | 78.6 | 62.1 | 82.0 | 96.0 | 7 | 80.2 | 10.1 |
| 12 wks test | 67.1 | 68.3 | 78.4 | 75.0 | | 80.8 | 86.0 | 6 | 75.9 | 7.3 |
| 14 wks test | 64.8 | 63.6 | 57.1 | 78.7 | | 79.6 | 76.0 | 6 | 70.0 | 9.4 |
| 16 wks test | | | | | | 79.2 | 74.2 | 2 | 76.7 | 3.5 |
| 10 wks control | 72.4 | 79.7 | 68.2 | 49.7 | 74.5 | 69.7 | 73.7 | 7 | 69.7 | 9.6 |

Note:
12-week data for subjects F and G are linearly extrapolated from 10 and 14 week data
Test units: Packed red cells were stored under oxygen depleted conditions at 4 C. in OFAS3 storage solution. At weeks 7 and 11, metabolic supplements were added at 4 C.
Control units: Packed red cells were stored in OFAS3 storage solution at 4 C. without oxygen depletion or metablic supplement additions.

Although the present invention describes in detail certain embodiments, it is understood that variations and modifications exist known to those skilled in the art that are within the invention. Accordingly, the present invention is intended to encompass all such alternatives, modifications and variations that are within the scope of the invention as set forth in the following claims.

What is claimed is:

1. A method for the storage of red blood cells comprising the steps of:
    mixing a red blood cell additive solution having a pH ranging from 5.5 to 6.5 with packed red blood cells creating a suspension of red blood cells;
    reducing the oxygen in said suspension of red blood cells to ≦10% of the level in whole blood; and
    storing said suspension of red blood cells under refrigerated, oxygen-depleted storage for a storage period.

2. A method according to claim 1, first comprising mixing whole blood with an anticoagulant solution, concentrating the red blood cells from said whole blood and separating the plasma thereby creating packed red blood cells.

3. A method according to claim 1, wherein said additive solution is wherein OFAS3 which comprises the following concentrations of about 0.5 to 4.0 mmole/liter of adenine, about 50 to 150 mmole/liter of dextrose, about 20 to 70 mmole/liter of mannitol, about 0 to 100 mmole/liter of NaCl and, about 2 to 20 mmole/liter of $NaH_2PO_4$.

4. A method according to claim 1, wherein said additive solution comprises about 2 mmole/liter adenine, about 110 mmole/liter dextrose, about 55 mmole/liter NaCl, and about 12 mmole/liter $NaH_2PO_4$.

5. A method according to claim 1, wherein said additive solution has an adjusted pH of 6.5.

6. The method of claim 1, wherein said suspension of red blood cells are continuously stored and maintained during said storage period.

7. The method of claim 1, wherein said suspension of stored red blood cells are stored at a refrigeration temperature of 4° C.

8. The method of claim 1, further comprising the step of addition of a metabolic supplement to said suspension of stored red blood cells at least once during refrigerated storage.

9. The method of claim 8, wherein said metabolic supplement comprises pyruvate, inosine, adenine and optionally dibasic sodium phosphate and/or monobasic sodium phosphate.

10. The method of claim 1, wherein said additive solution is AS-3 or EAS61.

* * * * *

UNITED STATES PATENT AND TRADEMARK OFFICE
CERTIFICATE OF CORRECTION

| | | |
|---|---|---|
| PATENT NO. | : 8,071,282 B2 | Page 1 of 1 |
| APPLICATION NO. | : 11/128576 | |
| DATED | : December 6, 2011 | |
| INVENTOR(S) | : Mark W. Bitensky et al. | |

It is certified that error appears in the above-identified patent and that said Letters Patent is hereby corrected as shown below:

On the title page, item (60), change "60/322,405" to --60/332,405--.

Signed and Sealed this
Twenty-seventh Day of May, 2014

Michelle K. Lee
*Deputy Director of the United States Patent and Trademark Office*

UNITED STATES PATENT AND TRADEMARK OFFICE
CERTIFICATE OF CORRECTION

Page 1 of 1

PATENT NO.       : 8,071,282 B2
APPLICATION NO.  : 11/128576
DATED            : December 6, 2011
INVENTOR(S)      : Mark W. Bitensky et al.

It is certified that error appears in the above-identified patent and that said Letters Patent is hereby corrected as shown below:

This certificate supersedes the Certificate of Correction issued on May 27, 2014. The certificate which issued on May 27, 2014 is vacated because there is no proper claim to 60/332,405 and there is no reference to the intermediate application 10/195,781 and is more than one year after the filing date of this application so benefit would not be proper. Therefore, no proper benefit claim has been presented in the application. The Certificate of Correction which issued on May 27, 2014 was published in error and should not have been issued for this patent.

Title Page, item (60) should read

-- (60) Provisional application No. 60/322,405, filed on Nov. 16, 2001. --.

Signed and Sealed this
Twenty-fifth Day of August, 2015

Michelle K. Lee
*Director of the United States Patent and Trademark Office*